United States Patent [19]
Cummings et al.

[11] Patent Number: 5,413,110
[45] Date of Patent: *May 9, 1995

[54] COMPUTER GATED POSITIVE EXPIRATORY PRESSURE METHOD

[75] Inventors: Charles C. Cummings, Towson, Md.; Robert I. Prince, Gainesville, Fla.

[73] Assignee: Puritan-Bennett Corporation, Kans.

[*] Notice: The portion of the term of this patent subsequent to Sep. 22, 2009 has been disclaimed.

[21] Appl. No.: 947,441

[22] Filed: Sep. 21, 1992

Related U.S. Application Data

[63] Continuation of Ser. No. 593,324, Oct. 1, 1990, Pat. No. 5,150,291, which is a continuation of Ser. No. 512,577, Apr. 20, 1990, abandoned, which is a continuation of Ser. No. 845,942, Mar. 31, 1986, abandoned.

[51] Int. Cl.$^6$ ............................................. A61M 16/00
[52] U.S. Cl. ............................. 128/696; 128/204.23; 128/205.24
[58] Field of Search ................... 128/670–671, 128/700, 716, 718–720, 696, 204.18, 204.23, 204.24, 205.19, 205.24

[56] References Cited

U.S. PATENT DOCUMENTS 4,074,710  2/1978  Tiep ................................. 128/716 X
5,020,516  6/1991  Biondi et al. ..................... 128/671 X

*Primary Examiner*—Angela D. Sykes
*Attorney, Agent, or Firm*—Fulwider Patton Lee & Utecht

[57] ABSTRACT

The computer gated positive expiratory pressure method alters pressure in a patient breathing pathway in a respiratory ventilator during specified periods of a patient's heart cycle. Heartbeats of a patient are detected in patient cardiac cycles, and an electrical heartbeat signal is generated in response to the heartbeats. In a presently preferred embodiment, the electrical heartbeat signal is squared to amplify the signal. A variable moment following a detected heartbeat is determined, and positive ventilation pressure in the patient breathing pathway is altered commencing at the variable moment following a detected heartbeat, for a variable time interval during selected cardiac cycles.

6 Claims, 1 Drawing Sheet

COMPUTER GATED POSITIVE EXPIRATORY PRESSURE METHOD This is a continuation of application Ser. No. 07/593,324, filed Oct. 1, 1990, now U.S. Pat. No. 5,150,291, which is a continuation of application Ser. No. 07/512,577, filed Apr. 20, 1990, now abandoned, which is a continuation of application Ser. No. 06/845,942, filed Mar. 31, 1986, now abandoned.

BACKGROUND

When breathing normally, one's diaphragm is dropped to increase one's thoracic cavity, thus creating a negative pressure in the thoracic cavity, relative to atmospheric pressure. Air is driven by the atmospheric pressure into the negative-pressure thoracic cavity. Many patients, such as victims of accidents suffering from shock, trauma or heart attack, may require a respirator or ventilator to aid breathing. Prior respirators used intermittent, positive pressure breaths to increase the pressure within a patient's lungs until filled. Air is expelled passively by the natural stiffness of the lungs.

Such respirators drive a positive pressure breath into the lungs which are already at atmospheric pressure. The pressure in the lungs is increased above atmospheric pressure, contrary to normal occurrence, which inhibits the heart's ability to pump blood. During normal respiration, negative thoracic pressure is developed upon inspiration of air, which aids in filling the heart with blood. The resultant pressure gradient (the relatively positive pressure in the periphery and negative pressure in the thorax) helps to fill the heart as it opens, subsequent to the heart's squeezing or pumping motion. If however, the pressure in the thoracic chamber is increased, as with respirators, the amount of blood returning or entering the heart is decreased. The heart also must squeeze against a higher pressure. A lower cardiac output results.

The common technique for improving arterial oxygen tension is the use of Positive-End-Expiratory Pressure (PEEP), where a low level of positive pressure is maintained in the airway between positive pressure breaths. PEEP uses a standard switch. A pressure signal applied to the valve controls the high or low pressure states of the valve. The low PEEP state is generated when the valve is fully open. A partial closing of the valve creates high intrathoracic pressure between breaths, as some air from the tidal volume is not allowed to escape. However, at 10 centimeters of water pressure of PEEP, cardiac output drops significantly. Intravenous fluids are used to increase intravascular volume in an effort to minimize this fall in cardiac output. The patient may already have compromised cardiac function, minimizing or negating the advantages of the intravascular volume increase. Additionally, patients requiring respirators typically lack adequate kidney function and cannot process the added fluids. If too much intravenous fluid is used, relative to the patient's ability (aided or not) to process the fluid, the fluid may enter the patient's lungs.

Positive inotropic agents are used to increase the squeeze of the heart to pump more blood. Obviously, the heart works harder than normal resulting in possible heart attacks or arrhythmias. Often, physicians will prescribe a combination of increased intravenous fluids and positive inotropic agents with PEEP.

Several investigators have evaluated the effect of cardiac cycle-specified, increases in thoracic pressure on cardiac output. They synchronized high frequency jet ventilation to various phases of the R-R interval. Carlson and Pinsky found that the cardiac depressant effect of positive pressure ventilation is minimized if the positive pressure pulsations are synchronized with diasrole. Otto and Tyson, however, found no significant changes in cardiac output while synchronizing positive pressure pulsations to various portions of the cardiac cycle.

Pinchak described the best frequency in high frequency jet ventilation. He also noticed rhythmic oscillations in pulmonary artery pressure (PAP) and also rhythmic changes in systemic blood pressure. A possible explanation for these oscillations is that the jet pulsations move in and out of synchrony with the heart rate. In evaluating his data it appears that when jet airway pressure peak occurred during early systole there was a high pulmonary artery pressure, and a low systemic blood pressure. While Pinchak does not comment on this, his recorded data show that pulmonary artery pressure was waxing and waning precisely opposite to the blood pressure. A plausible explanation is an increase in pulmonary artery pressure is simply a reflection of an increase in pulmonary vascular resistance which causes a decrement in left ventricular filling and thus decrease in systemic blood pressure secondary to a decrease in cardiac output. If the slight oscillations in the systemic blood pressure reflect oscillations in cardiac output, then Pinchak's study would support Pinsky and Carlson's work, suggesting that positive airway pressure is least detrimental during diastole.

SUMMARY OF THE INVENTION

The invention concerns a computer-gated, positive expiratory pressure system for supplementing positive end-expiratory pressure (PEEP) systems. The output of a cardiogram machine is amplified and squared, or an LED of a cardiogram machine is optically monitored, to determine an R-wave, or the beginning of electrical systole. A signal is fed to a multiplier where the R-R wave signal (period) is multiplied representing the duration of the R-R wave with a variable interval set by a physician. The resultant product (R-R wave times variable interval) is used to trigger a solenoid operated 3-way valve. The 3-way valve is normally closed to pass a positive pressure to a standard PEEP valve which functions normally. When triggered, the 3-way valve opens to allow a relatively low pressure to pass to the PEEP valve such that the PEEP valve creates a low pressure to the patient.

Thus, PEEP is removed for a variable time ratio immediately before a next heart beat. The PEEP valve is controlled by computer gating a 3-way valve to create pressure drops, allowing the heart to fill. Once the heart fills, PEEP is resumed without any detrimental effects. Respiration of the patient is coordinated with the patient's heart beat to maximize cardiac output. Additionally pressure can be replaced immediately after drop out in an effort to improve emptying of the heart.

DETAILED DESCRIPTION OF THE INVENTION

Figure 1:
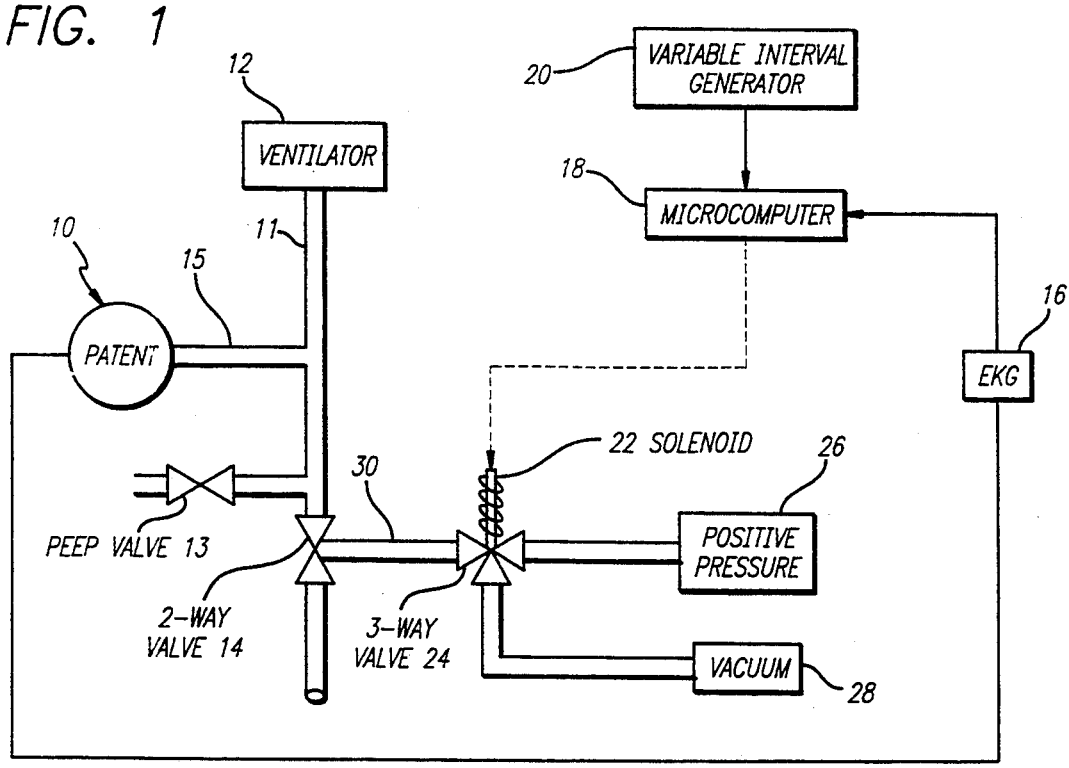
FIG. 1 is a schematic of the present invention in its environment.

The computer-gated, positive expiratory pressure system is shown in FIG. 1 in its environment, connected to a therapeutic device such as a PEEP system. A patient 10 is shown using a respirator or ventilator 12 via a standard expiratory (PEEP) valve 14. The PEEP valve 14 opens and closes to allow low and high pressures to the patient 10. In accordance with the present invention, the patient 10 is also connected to a cardiogram machine (EKG) 16. Successive heart beats are detected by the EKG 16 and a signal representing each beat is output to a microcomputer 18, the details of which are discussed regarding FIGS. 2 and 3. A variable interval is generated by generator 20 as a second input to the microcomputer 18, the value of the interval being set by the attending physician. The microcomputer 18 combines the variable interval signal from 20 and a value representing the period between successive heart beats from EKG 16 and generates a controlling output to a solenoid 22 of a 3-way valve 24. The 3-way valve 24 is connected by a first end to a positive pressure source 26. A second valve end is pneumatically connected to a low relative pressure 28, while a third end is connected to the PEEP valve 14 via which the patient 10 received the positive pressure breaths.

Under normal operation of the ventilator 12, the PEEP valve 14 is operated to allow alternate low and high positive pressure breaths (approximately 0.4 psi) from the ventilator 12 to pass directly to the patient 10. However, in response to the output of microcomputer 18, the solenoid 22 is energized to yield at output 30, a negative pressure from the low relative pressure source 28. The negative pressure output at 30 opens the PEEP valve 14. Because the PEEP valve 14 is fully opened, a low pressure is received by the patient 10 from the ventilator 12. The resultant low pressure, in accordance with the present invention, occurs just prior to a predicted heart beat to insure the heart, when filling., does not work against high pressures. PEEP systems per se too often generate high pressures when the heart beats, inhibiting heart filling and decreasing cardiac output.

Figure 2:
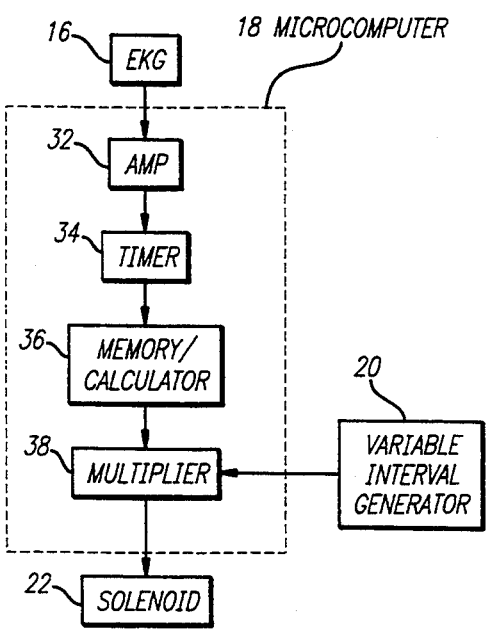
FIG. 2 is a block diagram of the FIG. 1 microcomputer contents, as connected to a 3-way valve.

In FIG. 2, the details of microcomputer 18 are evident. The output of EKG 16 is run through an operational amplifier 32 to a timer 34 which squares the amplified EKG signal to develop a series of electrical pulses corresponding to successive heart beats. The electrical pulses of timer 34 are received by memory/calculator 36 which determines a period representing the interval between successive heart beats. This period is used to predict a next heart beat so a low pressure is delivered to the patient slightly before and during this next heart beat. The variable interval generator 20 is set by the attending physician between 15 and 400 microseconds, for instance, by typical analog controls. The variable interval signal from 20 and the period signal from calculator 36 are used to generate a product in multiplier 38. The resultant product is used as a signal to energize the solenoid 32, to control 3-way valve 24.

In a normal state, 3-way valve 24 connects the positive pressure 26 to the output 30, putting PEEP valve 14 in a partially closed position. Thus, the Ventilator 12 can generate a high, positive pressure breath to the patient 10. However, assume the EKG 16 detects a heart beat each second. The EKG signal is amplified at 32, squared by timer 34, and the period of one second calculated in memory 36. If the variable interval generator is set by the physician for 0.8 second, multiplier 38 forms a product of the period and variable interval (1.0×0.8) equal to 0.8 seconds. Thus, 0.2 second before the next predicted, heart beat (0.8 second from the last heart beat) solenoid 22 is energized. The 3-way valve 24 now opens output 30 to the vacuum 28. Accordingly, a resultant negative pressure fully opens the PEEP valve 14 and a low pressure reaches the patient. Should the heart rate vary, the difference between predicted and actual heart beats will be detected and pulse timing corrected. The time duration of the pulse to the solenoid is controlled by a second timer (not shown).

Figure 3:
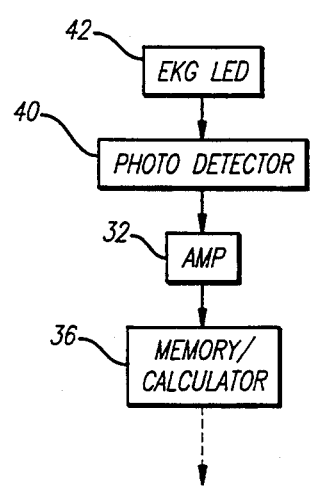
FIG. 3 reveals a second embodiment for detecting a heart beat interval.

FIG. 3 reveals a second embodiment for determining or sensing heart beats. A photodetector 40 is used to detect the blinking LED 42 which is typically part of a cardiogram machine. The photodetector 40, turning on and off with the flash of the LED 42, requires no timer or wave squarer, and thus is input directly to the amplifier 32 for subsequent processing in the manner of the FIG. 2 embodiment.

Other modifications are apparent to those skilled in the art which do not depart from the spirit of the present invention, the scope being defined by the appended claims. For instance, rather than use a microcomputer, a microprocessor (e.g. C 64 Commodore Computer) may be adapted and software developed to monitor and determine beat period, with a programmable variable interval for use by the physician.

What is claimed is:

1. A method for altering pressure in a patient breathing pathway in a respiratory ventilation apparatus during specified periods of a patient heart cycle, the respiratory ventilation apparatus having a ventilator and means for providing said patient breathing pathway with a positive ventilation pressure during a patient breath cycle, the steps of the method comprising:
   detecting heart beats in a plurality of patient cardiac cycles;
   generating an electrical heart beat signal in response to said heart beats, and amplifying said electrical heart beat signal;
   determining a variable moment following a detected heartbeat; and
   altering said positive ventilation pressure in said patient breathing pathway commencing at said variable moment following a detected heart beat for a variable time interval during selected cardiac cycles.

2. The method of claim 1, wherein said step of altering said positive ventilation pressure comprises providing a low positive ventilation pressure in said patient breathing pathway.

3. The method of claim 1, wherein said respiratory ventilation apparatus includes a control valve connected to said patient breathing pathway having open and closed positions in which said control valve induces alternating low and high positive ventilation pressures in said breathing pathway, respectively, and control means for generating a control signal for a predetermined period of time commencing at said variable moment during selected cardiac cycles of said patient for operation of said control valve, and said step of altering said positive ventilation pressure comprises generating said control signal for a predetermined period of time commencing at said variable moment during selected patient cardiac cycles, and opening said control valve responsive to said control signal to provide said low positive ventilation pressure in said patient breathing pathway.

4. The method of claim 1, wherein said step of determining said variable moment comprises determining a period of time between selected sequential patient heart beats, and multiplying a preselected multiplier value by said period of time between said selected sequential heart beats, said preselected multiplier value approximately corresponding to a computed fraction of said period of time between heart beats.

5. A method for altering pressure in a patient breathing pathway in a respiratory ventilation apparatus during specified periods of a patient heart cycle, the respiratory ventilation apparatus having a ventilator and means for providing said patient breathing pathway with a relatively high positive ventilation pressure and a relatively low positive ventilation pressure, the steps of the method comprising:

alternatingly providing said patient breathing pathway with a relatively high positive ventilation pressure and a relatively low positive ventilation pressure to produce a pressure or volume supported breath cycle;

detecting heart beats in a plurality of patient cardiac cycles;

producing a secondary relatively low positive ventilation pressure in said patient breathing pathway commencing at a variable moment following a detected heart beat for a variable time interval during selected cardiac cycles; and determining said variable moment by determining a period of time between selected sequential heart beats of said patient, and multiplying a preselected multiplier value by said period of time between said selected sequential heart beats, said preselected multiplier value approximately corresponding to a computed fraction of said period of time between heart beats.

6. The method of claim 5, wherein said ventilator includes control means for generating a control signal and control valve means connected to said patient breathing pathway having an open position in which said control valve means induces said relatively low pressure in said breathing pathway, and said step of producing said secondary relatively low positive ventilation pressure comprises generating a control signal for a predetermined period of time commencing at said variable moment during selected cardiac cycles of said patient, and opening said control valve means responsive to said control signal.

* * * * *